United States Patent [19]

Taylor et al.

[11] Patent Number: 4,508,923

[45] Date of Patent: Apr. 2, 1985

[54] OXIDATION OF HYDROCARBONS

[75] Inventors: Paul D. Taylor, Berwyn; Michael T. Mocella, West Chester, both of Pa.

[73] Assignee: Atlantic Richfield Company, Los Angeles, Calif.

[21] Appl. No.: 468,605

[22] Filed: Feb. 22, 1983

[51] Int. Cl.³ ............................................. C07C 45/53
[52] U.S. Cl. ................... 568/311; 568/342; 568/384; 568/570; 568/571; 568/575; 568/835; 568/840; 568/768
[58] Field of Search ............... 568/570, 571, 849, 835, 568/342, 384, 311, 798, 575, 840, 768

[56] References Cited

U.S. PATENT DOCUMENTS

| | | | |
|---|---|---|---|
| 3,055,840 | 9/1962 | Kach | 568/835 |
| 3,925,316 | 12/1975 | Brunie et al. | 568/342 |
| 3,927,108 | 12/1975 | van de Moesdijk et al. | 568/835 |
| 3,987,100 | 10/1976 | Barnette et al. | 568/570 |
| 4,042,630 | 9/1977 | Wolters et al. | 568/835 |
| 4,053,524 | 10/1977 | Stapp et al. | 568/835 |

*Primary Examiner*—James H. Reamer
*Attorney, Agent, or Firm*—MichAel S. Jarosz

[57] ABSTRACT

There is disclosed an improved process for oxidizing a hydrocarbon to produce a reaction mixture containing the corresponding organic hydroperoxide of said hydrocarbon and decomposing said hydroperoxide to provide a mixture containing reaction products of said decomposition reaction, including alcohol and/or ketone products, comprising effecting said oxidation and/or decomposition in the presence of a catalytic quantity of a catalyst system comprised of ruthenium and chromium.

19 Claims, No Drawings

OXIDATION OF HYDROCARBONS

BACKGROUND OF THE INVENTION

1. Field of the Invention

This invention relates to an improved process for the oxidation of hydrocarbons, particularly aliphatic and alicyclic hydrocarbons, to form the corresponding hydroperoxides. More particularly, the invention relates to an improved catalytic process for the production of alcohols and ketones wherein a hydrocarbon is oxidized in the presence of a molecular oxygen containing gas to produce a reaction mixture containing the corresponding hydroperoxides and the hydroperoxide is decomposed, the products of the decomposition generally comprise the alcohol and ketone. As is well known of the art, the products of such decomposition reactions are employable as obtained as commercial products, for example, tertiary butyl alcohol in the case of the decomposition of tertiary butyl hydroperoxide, or alternatively, may readily be converted by further reaction, as by oxidation, to derivatives thereof, for example, adipic acid, in the case of decomposition of cyclohexyl hydroperoxide producing a mixture of cyclohexanone and cyclohexanol.

2. Description of Prior Art

The oxidation a the number of aliphatic and alicyclic hydrocarbons to end product alcohols and ketones, optionally via hydroperoxide decomposition, is a well-known competitive, large-volume industrial practice. Experience in the operation of such processes, which are reflected in the disclosures of numerous patents and literature references, has indicated that the oxidation must be carried out at controlled conversion levels, for example, to minimize the formation of other undesirable oxidation products, some of which may have an adverse effect on acceptability in industrial usage directly or may have deleterious effects in the production of derivative products and/or of purity of the derivative products produced. Relatively minor process improvements, such as in the yield of the intermediate hydroperoxide, or in the conversion of the hydroperoxide to desired alcohol and ketone product, may result in highly beneficial cost advantages. Accordingly, there is a strong economic incentive to increase the efficiency of the oxidation process from which such products are obtained.

In U.S. Pat. No. 3,879,467 there is disclosed a process for the catalytic oxidation of certain hydrocarbons utilizing an organic hydroperoxide in the presence of a chromium catalyst to produce alcohols and ketones as the primary products. Also disclosed in this patent for this purpose are a number of other specific metal catalysts which resulted in low hydroperoxide conversions or low product yields, or both, or in instances where high conversions were noted, almost no product yields were obtained.

U.S. Pat. No. 3,530,185 discloses a process for the partial oxidation of cyclohexane employing a mixture of gases including molecular oxygen at controlled partial pressure and inert gas in the presence of a catalyst, such as a cobalt compound, which will cause decomposition of the intermediate cyclohexyl hydroperoxide to cyclohexanol and cyclohexanone.

U.S. Pat. No. 3,987,100 discloses cyclohexane oxidation in the presence of a binary catalyst system comprising specific amounts of chromium and cobalt to produce cyclohexyl hydroperoxide followed by decomposition thereof in the presence of said catalyst and recovering a product of cyclohexanone and cyclohexanol in specified ratio.

U.S. Pat. No. 3,925,316 discloses a process for the preparation of mixtures of cycloalkanols and cycloalkanones by heating cycloalkyl hydroperoxides in the presence of a soluble derivitive of ruthenium.

Certain forms of ruthenium have also been reported in recent publications in connection with cumene hydroperoxide decomposition studies. In this regard, attention is directed to "Use of the Proton NMR Relaxation Method to Study the Coordination of Cumene Hydroperoxide With Cobalt and Ruthenium Carboxylates", V. M. Nekipelov, Dokl. Akad. Nauk SSSR, V 261 (6), 1377–81 (1981); "NMR Studies of .Mu3-Oxotriruthenium Hexacarboxylate Cumene Hydroperoxide Interaction", A. M. Trzeciak, Oxid. Commun., V. 1 (4), p. 295–303 (1980); "Cumene Hydroperoxide Decomposition Reaction Catalyzed by Ruthenium (III) beta.-diketonates", A. M. Trzeciak, et al, React. Kinet. Catal. Lett., V. 12 (1–2), p. 121–5 (1981); and "Decomposition of Organic Hydroperoxides on Ruthenium .pi.-Complexes", Yu A. Aleksandrov, Ah. Obshch. Khim., V. 48 (9), p. 2142 (1978).

A significant step in the rather complicated overall oxidation process is the decomposition of the hydroperoxide, which is the subject of our co-pending application Ser. No. 462,261, filed of even date, entitled "Decomposition of Hydroperoxides in the Presence of Homogeneous Binary Catalysts", the disclosure of which is hereby incorporated by reference. Since the efficiency of the decomposition step contributes to the efficiency of the overall oxidation step, improvement in the decomposition of the hydroperoxide is an obvious desirable objective.

As is apparent to those skilled in the art, the hydroperoxide decomposition may be effected in various manner. Hence, the hydroperoxide may "self decompose", in which case all of the alcohols and ketone moieties produced are derived directly from the hydroperoxides. Alternatively, in the event a diluent and/or solvent is employed in the decomposition reaction, the hydroperoxide may also decompose by a reaction involving the hydrocarbon diluent/solvent which is converted to alcohol and ketone products. Under these circumstances the process is represented as being the reaction of one mole of the hydrocarbon starting material with one mole of the corresponding hydroperoxide to yield two moles of alcohol and/or ketone. In addition, since there is a build-up of liberated molecular oxygen as a result of decomposition of hydroperoxide, additional oxidation of the hydrocarbon diluent/solvent may be anticipated as a result of reaction of such liberated oxygen therewith.

The reaction of the diluent/solvent hydrocarbon results in higher conversions, in general, of the hydrocarbon starting material to the useful oxidation products that will be realized if the hydroperoxide decomposed by itself. Of particular advantage would be to increase the amount of alcohol and ketone product derived from the diluent/solvent by its oxidation with the hydroperoxide or liberated oxygen, without adversely affecting the yield of alcohol and ketone derived directly from the intermediate hydroperoxide.

Accordingly, improvements in the oxidation step as well as in the decomposition step of the process for producing alcohols and ketones from hydrocarbon feed materials are highly desirable objectives.

SUMMARY OF THE INVENTION

The present invention provides an improvement in the process for producing alcohols and ketones wherein hydrocarbon feed materials, such as aliphatic and alicyclic hydrocarbons, are oxidized in the presence of a molecular oxygen-containing gas to provide a reaction mixture containing the corresponding hydroperoxide and the hydroperoxide is decomposed in the presence of starting hydrocarbon feed to provide a mixture containing the desired alcohol and ketone products. The improvement comprises effecting the oxidation reaction by contacting the hydrocarbon feed material, illustratively an aliphatic or an alicyclic hydrocarbon, with a molecular oxygen containing gas, such as air, at a temperature of from about 50° C. to about 250° C., preferably between about 75° C. and 225° C. in the presence of a catalytic quantity of a homogeneous catalyst system comprising an admixture of ruthenium and chromium, thereby forming various oxidation reaction products, including the corresponding hydroperoxide of said hydrocarbon feed, alcohols, ketones, etc., and, optionally, conducting decomposition of the hydroperoxide by contacting a reaction mixture containing such hydroperoxide in unreacted hydrocarbon with a catalytic amount of said catalyst system at a temperature of from about 25° C. to about 250° C., and preferably betwen about 50° C. and 150° C., optionally in the presence of a molecular oxygen.

The advantages realized by use of the catalyst described, as compared with the use of chromium and/or ruthenium alone, include improved conversions of the hydrocarbons starting material to oxidation products, and of hydroperoxide to alcohol and ketone products; improved activity for organic hydroperoxide decomposition and selectivity to the desired alcohol and ketone products; and maintenance of stability of the catalyst system, as evidenced by substantial elimination of the formation of insoluble metalcontaining compositions.

DETAILED DESCRIPTION OF THE INVENTION

The catalyst system employed in the process of the present invention comprise an admixture of ruthenium and chromium compounds which are soluble or capable of being solubilized in the hydrocarbon feed to be oxidized, as well as in the hydroperoxide intermediate to be decomposed, i.e. the reaction mixture. Representative examples of ruthenium and chromium compounds employable in the process of the invention include ruthenium and chromium salts of carboxylic acids, salts of organic acids produced in the course of oxidation of the precursor hydrocarbon from which the organic hydroperoxide may have been obtained, carbonyls, sulfates, nitrates, halides, and organometalic compounds of those metals. Representative examples of ruthenium compounds include ruthenium maphthenate, ruthenium octoate, ruthenium laurate, ruthenium stearate, ruthenium linoleate, ruthenium acetylacetonate, ruthenium nitrate, ruthenium chloride, ruthenium sulfate and ruthenium carbonyl. Representative examples of chromium compounds include chromium naphthenate, chromium octoate, chromium laurate, chromium palmatate, chromium stearate, chromium linoleate, chromium acetylacetonate, chromium nitrate, chromium chloride, chromium sulfate and chromium carbonyl.

Representative examples of organic acids which may be produced in the course of oxidation of the hydrocarbon starting material precursor to the organic hydroperoxide include: acetic, formic, propionic, isobutyric, caproic, valeric, adipic, glutaric, hydroxycaproic and benzoic acids.

The hydrocarbon feed materials employed in the process of the present invention comprise both aliphatic and alicyclic hydrocarbons. Suitable aliphatic compounds include both paraffinic and olefinic hydrocarbons, such as propylene, n-butane, isobutane, isobutylene, 1-butene, and hexadecane, while the alicyclic compounds include both saturated polycyclic ring compounds such as decalin and non-aromatic unsaturated and saturated ring compounds such as cyclohexene and cyclohexane. These compounds may be substituted by groups which would be inert to oxidation under conditions of the process, as for example, nitro, nitrile, phenyl, sulfone and carboxylic acid groups. In general, the aliphatic and alicyclic hydrocarbons suitable for feed reactant in the process of the present invention contain from 2 to 25 carbon atoms and preferably 3 to 10 carbon atoms. It is noted that in the saturated compounds, the secondary and/or tertiary carbon atoms are more readily oxidized in the process, while in unsaturated hydrocarbons, those carbon atoms which are adjacent to a double bond, whether they be primary, secondary or tertiary, will be readily oxidized. As previously indicated, processes for the oxidation of hydrocarbons contemplated herein are well described in the literature. The process of the present invention may be employed in such manner as to carry out the oxidation and/or decomposition reactions only, or in combination, sequentially and/or in series. Hence, for example, hydrocarbon oxidation and corresponding hydrocarbon hydroperoxide decomposition may be conducted in separate stages or in the same stage, regardless of whether or not the oxidation is conducted in a series of zones. It is to be understood that, except for details specified, the oxidation and decomposition steps are effected in conventional manner.

The distribution of products from the oxidation of the hydrocarbon feed depends upon both temperature and percent conversion of the hydrocarbon to products. Thus, within the given temperature range indicated, in general, the lower the temperature, the greater the amount of hydroperoxide which will be formed as the principle product. As the temperature is increased, it is found that the oxidation of primary carbon atoms leads principally to the production of by-product aldehydes and acids; the oxidation of secondary carbon atoms leads principally to the production of ketones and alcohols; while the oxidation of tertiary carbon atoms generally results either in decomposition of the hydroperoxide to form an alcohol, or in chain scission to yield a ketone and an alcohol as the principal products. Oxidation reaction conditions for production of desired product depend on factors such as the particular catalyst, conversion desired, reaction temperature and time, as well as upon the starting material employed. Thus, for example, the oxidation of isobutane in accordance with the present invention at temperatures between 100° C. and 160° C. will provide the corresponding hydroperoxide, while the same oxidation carried out at more elevated temperatures of between about 190° C. and 250° C. will result in acetone and methyl alcohol as the principal products.

The oxidation reaction of the process of the present invention, utilizing the aforedescribed catalyst system, is conveniently carried out by the rapid passage of a molecular oxygen containing gas, such as air, through a suitable reactor, to which there has been charged a mixture of the hydrocarbon substrate and catalyst system. The molecular oxygen containing gas is brought into intimate contact with the liquid phase, for example, by the use of high-speed stirrers, nozzles, or the like in conventional manner. The concentration of the catalyst system in the liquid phase, in general, may vary widely, depending upon the nature and amount of material to be oxidized. In general, however, the quantity of catalyst employed in the oxidation step will vary from about 0.01 to about 1000 ppm of metal (or mixed metal), and greater, preferably from about 1 to 100 ppm, by weight, in the total mixture; the catalyst concentration is also dependent upon temperature and conversion desired. Moreover, with respect to the nature of catalyst employed, the proportion of chromium to ruthenium may range from 0.5:1 to 10:1 and higher, in achieving the objectives of the process. If desired, pressures from about 1 to 100 atmospheres, preferably between about 2 and 50 atmospheres, may be employed to maintain the liquid phase.

To moderate the decomposition reaction, the process is usually carried out in a suitable diluent/solvent. Suitable diluents include alkanes, such as hexane, heptane and hexane; cycloalkanes, such as cyclopentane, methylcyclopentane, and cyclohexane; aromatic hydrocarbons, such as benzene, toluene, and xylene; and mixtures of such hydrocarbons with aromatic halides or ethers such as chlorobenzene or diphenyl ether. To facilitate effecting the reaction, the solvent employed is the hydrocarbon from which the hydroperoxide may have been derived by oxidation, i.e. precursor starting materials, for example, such as cyclohexane in the case where the desired hydroperoxide is cyclohexyl hydroperoxide.

The rate of input of molecular oxygen containing gas will depend upon the temperature and pressure utilized during the oxidation period, and heat removal limitations since these oxidations are highly exothermic. Normally there is provided at least an amount theoretically sufficient substantially to convert the starting material to the corresponding oxidation product, and preferably, in slight excess of this amount. As previously indicated, molecular oxygen is also obtained as liberated oxygen resulting from the decomposition reaction to be conducted. It has been found that a flow rate ranging from about 10 to 1,000 liters per liter of solution per hour is generally sufficient for most conversions. Any unreacted oxygen may be recycled to the reactor.

The reaction is generally complete in from about 1 to 10 hours, depending upon the amount of substrate employed, particular catalyst, conversion desired and reaction temperature employed. Preferably, the reaction is terminated after a period of about 1 to 4 hours and the products are separated from the reactants by conventional means such as by distillation. The catalyst retained in the distilland also may be recovered in conventional manner or recycled to the oxidation reaction.

If desired, small amounts of hydroperoxide may be introduced into the oxidation reaction medium to act as reaction initiator. Thus, for example, when isobutane is being oxidized, minor amounts, up to about 3%, by weight of the reaction mixture, of tertiary butyl hydroperoxide may be added in order to initiate the reaction.

The concentration of hydroperoxide in the reaction mixture obtained from the oxidation reaction, i.e. hydroperoxide feed of the decomposition reaction, may vary widely and, in general, ranges from about 1% to about 80%, by weight and preferably, from about 2% to about 60% by weight, based on the total reaction mixture. The catalyst concentration in the total mixture will normally range from about 0.01 up to about 5,000 ppm of metal and greater, and preferably from about 1 to about 100 ppm. Lower catalyst concentrations are employed normally at higher temperatures. The reaction time will depend on the temperature and the catalyst concentration and will usually range from about 0.1 to about 5 hours, preferably from about 0.1 to about 2 hours. Although longer reaction times may be employed, in general no particular advantage is achieved thereby. Generally, the temperature in the decomposition reaction of the process of the invention will range from about 20° C. to about 200° C., preferably from about 50° to about 150° C. Pressures of from about 1 to about 100 atmospheres, preferably of from about 2 to about 50 atmospheres, may be employed in order to maintain the reaction in liquid phase.

Although the hydroperoxide and hydrocarbon starting material/solvent will be supplied to the hydroperoxide decomposition reactor as the liquid effluent obtained from the primary oxidation zone, it should be appreciated that this reaction mixture will also contain final desired alcohol and ketone products, along with minor amounts of other oxidation products and catalyst remaining from the oxidation reaction. However, if desired, a solution of pure hydroperoxide and solvent hydrocarbon may also be employed as the starting material for the decomposition step.

In the process of the present invention, decomposition of hydroperoxide may be effected in the presence or absence of added molecular oxygen. It is to be appreciated that oxygen may additionally be derived as liberated oxygen as a result of decomposition of previously formed hydroperoxide. It has also been found that when the hydroperoxide is decomposed in a stage separate from oxidation and at a lower temperature, the yield of alcohol and ketone from hydrocarbon participation in the decomposition of the hydroperoxide may be increased, without significantly reducing the yield of alcohol and ketone obtained directly from hydroperoxide decomposition, simply by adding molecular oxygen to the decomposition reaction mixture. Alternatively, the hydroperoxide decomposition may be effected at an increased rate to yield excessive quantities of liberated molecular oxygen which will provide the same result as the addition of molecular oxygen, as previously explained. The introduction of oxygen may be generally carried out in any convenient manner to permit control of the concentration of oxygen desired. Hence, oxygen may be supplied as air, as air enriched with added oxygen, or as air or molecular oxygen diluted with an inert gas such as nitrogen or argon.

Any amount of added oxygen will bring about increased production of alcohol and ketone products via hydrocarbon oxidation. The mole ratio of oxygen to hydroperoxide may also vary widely and generally will range from about 0.1 to about 20. The preferred range of oxygen/hydroperoxide mole ratio will range from about 0.5 to about 5 at which significant increases may be noted.

The time required for the decomposition reaction in the presence of molecular oxygen will depend on the hydroperoxide concentration, the nature of catalyst, and catalyst concentration, the oxygen/hydroperoxide mole ratio and the reaction temperature. Normally the reaction time will vary between about 0.1 hours and 5 hours and preferably between about 0.1 hours and 2 hours. When oxygen is used during the decomposition step, the temperature will vary from about 50° to about 250° C. and will preferably range from about 85° to about 150° C.

The process of the present invention may be carried out by effecting the oxidation and decomposition steps concurrently in the same stage or the oxidation and decomposition reactions may be carried out in separate stages. The process of the invention may be effected by a batch method or continuous method, although it is preferred to operate the process in a continuous manner in the presence of added molecular oxygen, as described above.

The invention may be illustrated by the following examples in which all temperatures are in degrees Centigrade and all percentages are by weight unless otherwise specified.

EXAMPLE 1

The apparatus to be used for effecting oxidation consists of a stainless steel autoclave having a volume of approximately 250 cc and usable at internal pressures up to about 5000 psig equipped with a magnetic stirrer, an inlet tube attached to a pressure guage, an outlet tube for liquid samples and an outlet tube for gas samples. The autoclave is equipped with a pressure-relief valve and heating is provided externally be means of a reactor jacket connected to an oil pump/bath regulated by a heater control. Internal cooling coils are provided to quench the reaction contents at the end of the run or in the event the reaction exothermed. Temperatures are measured with a resistence thermometer.

The reactor is charged with 10 ppm of an equimolar mixture of ruthenium acetylacetonate and chromium acetylacetonoate in 150 cc of isobutane at about 50 atmospheres of air flowing continuously at about 10 liters/hour (stp). With continuous stirring throughout the run, the contents of the reactor are brought to a temperature of about 150°, at which point evidence of an exothermic reaction is noted. After about 300 mins. when the molecular oxygen consumption indicates that about 20% of the isobutane is converted to products, the reactor is cooled and opened for recovery of the products thereof. Gas liquid analysis of the liquid reaction product shows that the major product is tertiary butyl alcohol with minor amounts of tertiary butyl hydroperoxide, methyl alcohol, ditertiary butyl peroxide and acetone.

EXAMPLE 1(A)

Control Experiment with Ruthenium Acetylacetonate

The procedure of Example 1 is repeated except that 10 ppm of ruthenium acetylacetonate is used. A precipitate is found in the reactor after completion of the run indicating that a good portion of the ruthenium precipitates. Gas liquid chromatography analysis of the reaction product shows that only about 60% of the tertiary butyl hydroperoxide produced is decomposed in the control run with ruthenium acetylacetonate, compared with essentially complete decomposition when the mixture or ruthenium and chromium acetylacetonates is used.

The results of this experiment show that the mixture of ruthenium and chromium acetylacetonates is a better catalyst than ruthenium acetylacetonate alone for the decomposition of tertiary butyl hydroperoxide and and that the mixture of ruthenium and chromium acetylacetonates is a stable catalyst system for effecting the decomposition reaction.

EXAMPLE 2

The reactor employed in Example 1 is charged with 100 cc of cyclohexane, 10 ppm of a equimolar mixture of ruthenium acetylacetonate and chromium acetylacetonate. The reactor is sealed and the reaction mixture is heated at 140° for 300 minutes with stirring to obtain a product mixture which, when analyzed by gas liquid chromotograph, shows the presence of 65% of cyclohexanone and 25% of cyclohexanol. The concentration of cyclohexyl hydroperoxide is 4%, corresponding to a practically complete conversion of the cyclic $C_6$ moiety of cyclohexyl hydroperoxide to cyclohexanone and cyclohexanol.

EXAMPLES 3 THROUGH 8

Employing the reactor described in Example 1 various catalysts of the invention are used to decompose cyclohexyl hydroperoxide prepared by oxidizing cyclohexane as in Example 2 without the decomposition catalyst being present during the oxidation. The reactor is pressurized with nitrogen to 500 psig to minimize the vaporization of cyclohexane and dilute the liberated oxygen. The results and details of these examples are set forth in Table I below.

TABLE I

| Example | Catalyst | ppm | Temperature | Hydroperoxide Decomposed After 120 minutes |
|---|---|---|---|---|
| 3 | chromium octoate and ruthenium octoate | 10<br>10 | 80 | 97 |
| 4 | chromium octoate and ruthenium octoate | 10<br>3 | 120 | 99 |
| 5 | chromium laurate and ruthenium laurate | 20<br>20 | 70 | 95 |
| 6 | chromium laurate and ruthenium laurate | 20<br>5 | 100 | 98 |
| 7 | chromium stearate and ruthenium stearate | 10<br>10 | 80 | 96 |
| 8 | chromium stearate and ruthenium stearate | 50<br>50 | 60 | 94 |

EXAMPLES 9 THROUGH 14

By using a procedure similar to that described in Examples 3–8 with exceptions noted below, catalysts of the invention (compared with control catalysts) are used to decompose tertiary butyl hydroperoxide in an oxidation mixture obtained from plant operation. The oxidation mixture contains approximately 42 parts of tertiary butyl hydroperoxide, 56 parts of tertiary butyl alcohol and 2 parts of a crude mixture comprised of low molecular weight oxygen-containing liquids. The reactor contents are heated to a temperature of about 78° C., and held thereat for a period of two hours. Liquid samples are withdrawn after the indicated period and analyzed by gas-liquid chromatography. Table II sets forth the results of the decomposition reaction:

TABLE II

| Example No. | Metal Salt Catalyst* | TBHP Decomposition (%) | Physical Characteristics of Reaction Product |
| --- | --- | --- | --- |
| 9 | Chromium (III) | 4.3 | clear, deep yellow solution |
| 10 | Cobalt (II) | 37.4 | turbid, pink solution containing precipitated metal |
| 11 | Manganese (II) | 16.9 | turbid, pinkish solution containing white precipitate |
| 12 | Ruthenium (III) | 99.0 | turbid, green solution containing grey precipitate |
| 13 | Equimolar mixture of: Ruthenium (III) and Chromium (III) | 96.6 | clear yellow solution with no precipitate |
| 14 | Equimolar mixture of: Cobalt (II) and Chromium (III) | 48.1 | clear yellow solution |

*As 100 ppm of acetylacetonoate complex

The results of the experiments set forth in Table II above demonstrate the superior activity of ruthenium for decomposition of tertiary butyl hydroperoxide and that equimolar admixtures of ruthenium and chromium provide a stable catalyst system for the decomposition of hydroperoxides while maintaining high activity for decomposition reaction.

We claim:

1. In a process for producing a mixture containing decomposition products of an organic hydroperoxide wherein a hydrocarbon is oxidized in the presence of a molecular oxygen containing gas to provide a reation mixture containing the corresponding hydroperoxide of said hydrocarbon and said hydroperoxide is decomposed in the presence of starting hydrocarbon to provide a mixture containing reaction products of such decomposition reaction, including an alcohol and/or ketone products, the improvement which comprises conducting the oxidation reaction by contacting the hydrocarbon with a molecular oxygen containing gas at a temperature of from about 50° C. to about 250° C. in the presence of a catalytic amount of an admixture of chromium and ruthenium compounds which are soluble in said reaction mixture, and conducting the decomposition reaction by contacting a reaction mixture containing the hydroperoxide of the hydrocarbon starting material at a temperature of from about 25° C. to about 250° C. in the presence of a diluent with a catalytic amount of said catalyst admixture, optionally in the presence of a molecular oxygen containing gas.

2. A process for the oxidation of a hydrocarbon to produce a hydroperoxide-containing reaction mixture which comprises contacting said hydrocarbon with a molecular oxygen containing gas at a temperature of from about 25° C. to about 250° C. in the presence of a catalytic quantity of an admixture of chromium and ruthenium compounds which are soluble in said reaction mixture.

3. The process of claim 1 wherein the catalyst admixture present in the oxidation step is in an amount of from about 0.01 ppm to 1,000 ppm ruthenium and from about 0.01 ppm to 1,000 ppm of chromium.

4. The process of claim 3 wherein the diluent is the hydrocarbon subjected to oxidation in the oxidation step of the reaction.

5. The process of claim 3 wherein the ruthenium and chromium catalyst is present in the form of at least one salt of a carboxylic acid.

6. The process of claim 3 wherein the ruthenium and chromium are present in the form of nitrate salts.

7. The process of claim 5 wherein each of ruthenium and chromium are present in the form of acetate salts.

8. The process of claim 7 wherein the hydrocarbon is isobutane.

9. The process of claim 8 wherein the hydrocarbon is cyclohexane.

10. The process of claim 8 wherein the hydrocarbon is cumene.

11. The process of claim 8 wherein the hydrocarbon is ethylbenzene.

12. The process of claim 2 wherein the catalyst admixture is present in an amount of from about 0.01 ppm to 1,000 ppm of ruthenium and from about 0.01 ppm to 1,000 ppm of chromium.

13. The process of claim 12 wherein the ruthenium and chromium catalysts are present in the form of at least one salt of a carboxylic acid.

14. The process of claim 12 wherein the ruthenium and chromium are present in the form of nitrate salts.

15. The process of claim 12 wherein each of ruthenium and chromium are present in the form of acetate salts.

16. The process of claim 12 wherein the hydrocarbon is isobutane.

17. The process of claim 12 wherein the hydrocarbon is cyclohexane.

18. The process of claim 12 wherein the hydrocarbon is cumene.

19. The process of claim 12 wherein the hydrocarbon is ethylbenzene.

* * * * *